US011369500B2

(12) United States Patent
Pathak et al.

(10) Patent No.: US 11,369,500 B2
(45) Date of Patent: *Jun. 28, 2022

(54) HANDHELD ARTICULATED USER-ASSISTIVE DEVICE WITH BEHAVIOR CONTROL MODES

(71) Applicant: Verily Life Sciences LLC, South San Francisco, CA (US)

(72) Inventors: Anupam J. Pathak, Mountain View, CA (US); Dylan Owens, Sunnyvale, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/539,524

(22) Filed: Aug. 13, 2019

(65) Prior Publication Data

US 2019/0365551 A1 Dec. 5, 2019

Related U.S. Application Data

(62) Division of application No. 15/583,482, filed on May 1, 2017, now Pat. No. 10,420,663.

(51) Int. Cl.
*A61F 4/00* (2006.01)
*A61B 5/11* (2006.01)
(Continued)

(52) U.S. Cl.
CPC ............ *A61F 4/00* (2013.01); *A61B 5/1114* (2013.01); *A61H 1/00* (2013.01); *G06F 3/017* (2013.01);
(Continued)

(58) Field of Classification Search
CPC .... A47G 23/02; A47J 43/288; A46B 15/0004; A46B 2200/1066; A46B 9/021;
(Continued)

(56) References Cited

U.S. PATENT DOCUMENTS

| 3,711,638 A | 1/1973 | Davies |
| 4,479,797 A | 10/1984 | Kobayashi et al. |

(Continued)

FOREIGN PATENT DOCUMENTS

| AT | 411 011 B | 9/2003 |
| CN | 2824877 Y | 10/2006 |

(Continued)

OTHER PUBLICATIONS

Chinese Office Action, dated Aug. 24, 2021, in corresponding Chinese Patent Application No. 201880028557.2, 7 pages.

(Continued)

*Primary Examiner* — Christie L Bahena
(74) *Attorney, Agent, or Firm* — Christensen O'Connor Johnson Kindness PLLC

(57) ABSTRACT

A handheld tool includes a handle; an implement mount configured to detachably accept and to rigidly hold a user-assistive implement; an actuator assembly mounted to the handle to physically manipulate the implement mount relative to the handle; a first sensor disposed to sense an orientation of the handle; a second sensor disposed to sense an orientation of the user-assistive implement; a controller disposed in or on the handle and coupled to the actuator assembly and the first and second sensors; and memory coupled to the controller. The memory stores instructions for identifying a type of the user-assistive implement attached to the implement mount, selecting a behavior routine based upon the type of the user-assistive implement identified, and manipulating the user-assistive implement relative to the handle according to the behavior routine to aid performance of a task with the handheld tool.

19 Claims, 11 Drawing Sheets

(51) Int. Cl.
| | |
|---|---|
| *A61H 1/00* | (2006.01) |
| *G06F 3/01* | (2006.01) |
| *A46B 15/00* | (2006.01) |
| *A47J 43/28* | (2006.01) |
| *A47G 23/02* | (2006.01) |

(52) U.S. Cl.
CPC ....... *A46B 15/0002* (2013.01); *A46B 15/0004* (2013.01); *A46B 2200/1046* (2013.01); *A46B 2200/1066* (2013.01); *A47G 23/02* (2013.01); *A47J 43/288* (2013.01); *A61B 5/1101* (2013.01); *A61B 2201/0165* (2013.01); *A61H 2201/12* (2013.01); *A61H 2201/50* (2013.01); *A61H 2201/503* (2013.01); *A61H 2201/5058* (2013.01)

(58) Field of Classification Search
CPC .......... A61F 2/588; A61F 4/00; A61B 5/1101; A61B 5/1114; A61B 5/6887; A61H 1/00
See application file for complete search history.

(56) References Cited

U.S. PATENT DOCUMENTS

| | | | |
|---|---|---|---|
| 4,766,708 A | 8/1988 | Sing | |
| 4,784,120 A | 11/1988 | Thomas | |
| 5,148,715 A | 9/1992 | Blaser et al. | |
| 5,316,479 A | 5/1994 | Wong et al. | |
| 5,562,707 A | 10/1996 | Prochazka et al. | |
| 5,691,898 A | 11/1997 | Rosenberg et al. | |
| 5,934,250 A | 8/1999 | Fujikawa et al. | |
| 6,234,045 B1 | 5/2001 | Kaiser | |
| 6,238,384 B1 | 5/2001 | Peer | |
| 6,458,089 B1 | 10/2002 | Ziv-Av | |
| 6,547,782 B1 | 4/2003 | Taylor | |
| 6,695,794 B2 | 2/2004 | Kaiser et al. | |
| 6,697,048 B2 | 2/2004 | Rosenberg et al. | |
| 6,697,748 B1 | 2/2004 | Rosenberg et al. | |
| 6,704,001 B1 | 3/2004 | Schena et al. | |
| 6,704,002 B1 | 3/2004 | Martin et al. | |
| 6,730,049 B2 | 5/2004 | Kalvert | |
| 6,740,123 B2 | 5/2004 | Davalli et al. | |
| 6,743,187 B2 | 6/2004 | Solomon et al. | |
| 6,946,812 B1 | 9/2005 | Martin et al. | |
| 7,106,313 B2 | 9/2006 | Schena et al. | |
| 7,224,642 B1 | 5/2007 | Tran et al. | |
| 7,725,175 B2 | 5/2010 | Koeneman et al. | |
| 7,883,479 B1 | 2/2011 | Stanley et al. | |
| 8,286,723 B2 | 10/2012 | Puzio et al. | |
| 8,308,664 B2 | 11/2012 | Pathak et al. | |
| 8,494,507 B1 | 7/2013 | Tedesco et al. | |
| 8,585,620 B2 | 11/2013 | McBean et al. | |
| 8,679,040 B2 | 3/2014 | Horst | |
| 9,074,847 B1 | 7/2015 | Sullivan et al. | |
| 9,144,476 B2 | 9/2015 | Iwahori et al. | |
| 2001/0012932 A1 | 8/2001 | Peer | |
| 2003/0006357 A1 | 1/2003 | Kaiser et al. | |
| 2003/0036805 A1 | 2/2003 | Senior | |
| 2003/0209678 A1 | 11/2003 | Pease | |
| 2005/0113652 A1 | 5/2005 | Stark et al. | |
| 2006/0044942 A1 | 3/2006 | Brinn et al. | |
| 2006/0241510 A1 | 10/2006 | Halperin et al. | |
| 2007/0050139 A1 | 3/2007 | Sidman | |
| 2007/0109783 A1 | 5/2007 | Wilson et al. | |
| 2007/0270784 A1 | 11/2007 | Smith et al. | |
| 2009/0031839 A1 | 2/2009 | Shimizu et al. | |
| 2009/0173351 A1 | 7/2009 | Sahin et al. | |
| 2009/0203972 A1 | 8/2009 | Heneghan et al. | |
| 2009/0227925 A1 | 9/2009 | McBean et al. | |
| 2009/0254003 A1 | 10/2009 | Buckman | |
| 2009/0276058 A1 | 11/2009 | Ueda et al. | |
| 2010/0013860 A1 | 1/2010 | Mandella et al. | |
| 2010/0036384 A1 | 2/2010 | Gorek et al. | |
| 2010/0079101 A1 | 4/2010 | Sidman | |
| 2010/0130873 A1 | 5/2010 | Yuen et al. | |
| 2010/0198362 A1 | 8/2010 | Puchhammer | |
| 2010/0228362 A1 | 9/2010 | Pathak et al. | |
| 2010/0274365 A1 | 10/2010 | Evans et al. | |
| 2011/0041269 A1 | 2/2011 | Iwahori | |
| 2011/0112442 A1 | 5/2011 | Meger et al. | |
| 2012/0139456 A1 | 6/2012 | Takano et al. | |
| 2012/0179075 A1 | 7/2012 | Perry et al. | |
| 2012/0249310 A1 | 10/2012 | Hotaling | |
| 2013/0060124 A1 | 3/2013 | Zietsma | |
| 2013/0060278 A1 | 3/2013 | Bozung et al. | |
| 2013/0118320 A1 | 5/2013 | Richardson | |
| 2013/0123666 A1 | 5/2013 | Giuffrida et al. | |
| 2013/0123684 A1 | 5/2013 | Giuffrida et al. | |
| 2013/0255980 A1 | 10/2013 | Linehan et al. | |
| 2013/0275779 A1 | 10/2013 | He | |
| 2013/0297022 A1 | 11/2013 | Pathak | |
| 2014/0052275 A1 | 2/2014 | Pathak | |
| 2014/0171834 A1 | 6/2014 | DeGoede et al. | |
| 2014/0257047 A1 | 9/2014 | Sillay et al. | |
| 2014/0257141 A1 | 9/2014 | Giuffrida et al. | |
| 2014/0303605 A1 | 10/2014 | Boyden et al. | |
| 2014/0303660 A1 | 10/2014 | Boyden et al. | |
| 2015/0053737 A1 | 2/2015 | Leimbach et al. | |
| 2015/0054633 A1 | 2/2015 | Saddik et al. | |
| 2015/0076209 A1 | 3/2015 | Shelton, IV et al. | |
| 2015/0300394 A1 | 10/2015 | Pathak | |
| 2016/0242679 A1 | 8/2016 | Pathak et al. | |
| 2017/0100272 A1 | 4/2017 | Pathak et al. | |
| 2018/0146960 A1* | 5/2018 | Shelton, IV | ............ G06F 21/60 |

FOREIGN PATENT DOCUMENTS

| | | |
|---|---|---|
| CN | 203646979 U | 6/2014 |
| CN | 106361479 A | 2/2017 |
| JP | 2008-67936 A | 3/2008 |
| JP | 2008-238338 A | 10/2008 |
| JP | 2010-118798 A | 5/2010 |
| KR | 101659554 B1 | 9/2016 |
| WO | 00/052355 A1 | 9/2000 |
| WO | 00/78263 A2 | 12/2000 |
| WO | 2013/049020 A1 | 4/2013 |
| WO | 2014/113813 A1 | 7/2014 |
| WO | 2015/003133 A1 | 1/2015 |

OTHER PUBLICATIONS

Ahmad Anouti, et al., "Tremor Disorders Diagnosis and Management," Western Journal of Medicine 162(6):510-513, 1995.
AU 2012316278—Australian Examination Report, dated Jul. 24, 2014, 3 pages.
AU 2012316278—Australian Notice of Acceptance, dated Jan. 15, 2015, 2 pages.
AU 2012316278—Australian Notice of Grant, dated May 14, 2015, 2 pages.
Cameron N. Riviere, et al., "Toward Active Tremor Canceling in Handheld Microsurgical Instruments," IEEE Transactions on Robotics and Automation, vol. 19, No. 5, Oct. 2003, pp. 793-800.
Caroline GL Cao, et al., "Robotics in Healthcare: HF Issues in Surgery," 2007, Online paper, <http://ase. tufls.edu/mechanical/EREL/Publications/D-4.pdf>, 33 pages.
CN 2012-80047035.X—First Chinese Office Action, with English Translation, dated Apr. 28, 2015, 10 pages.
CN 2012-80047035.X—Second Chinese Office Action, with English Translation, dated Sep. 14, 2015, 11 pages.
CN 201280047035X—Third Office Action with English translation, dated Feb. 26, 2016, 8 pages.
DC-Micromotors, Application Datasheet, 0615 4.5S. 2010; 1 page available from: http://www.micromo.com.
Deuschl, G. et al., "Treatment of Patients with Essential Tremor," Lancet Neural 10:148-161, 2011.
Diamond, A., et al., "The effect of deep brain stimulation on quality of life in movement disorders," Journal of Neurology, Neurosurgery & Psychiatry 76(9):1188-1193, 2005.
E. Rocon, et al., "Rehabilitation Robotics: a Wearable Exo-Skeleton for Tremor Assessment and Suppression," Proceedings of the 2005 IEEE International Conference on Robotics and Automation, 2005, pp. 2271-2276.

(56) References Cited

OTHER PUBLICATIONS

E. Rocon, et al., "Theoretical Control Discussion on Tremor Suppression via Biomechanical Loading," 2003, 5 pages.
Eduardo Rocon, et al., "Mechanical suppression of essential tremor," The Cerebellum 6(1):73-78, 2007.
EP 12834632.7—European Search Report, dated Jun. 10, 2015, 5 pages.
EP 12834632.7—Examination Report, dated Oct. 18, 2016, 5 pages.
EP 16202985.4—Extended European Search Report, dated Mar. 23, 2017, 7 pages.
Great Lakes Neurotechnologies, Press Release "Great Lakes Neurotechnologies Awarded Patent for Sensor Based Continuous Parkinsons Assessment During Daily Activities," Dec. 3, 2013, <www.glneurotech.com>, 2 pages.
International Search Report and Written Opinion from the International Searching Authority dated Aug. 2, 2018, for International Application No. PCT/US2018/023859, filed Mar. 22, 2018, 6 pages.
JP 2014-533640—First Japanese Office Action, dated Mar. 31, 2015, 5 pages.
JP 2014-533640—Notice of Allowance, dated Dec. 2, 2014, 3 pages.
JP 2016-000701—First Office Action, with English Translation, 15 pages, dated Jan. 10, 2017.
Kostikis, N. et al.—"Smartphone-based evalution of parkinsonian hand tremor: Quantitative measurements vs clinical assessment scores," 2014 36th Annual International Conference of the IEEE Engineering in Medicine and Biology Society, IEEE, Aug. 26, 2014, pp. 906-909.
KR 10-2014-7011131—First Office Action, with English translation, dated Aug. 20, 2015, 7 pages.
Louis, E.D., "Essential Tremor," Handbook of Clinical Neurology, vol. 100, 2011, pp. 433-448.
Louis, E.D., et al., "Correlates of Functional Disability in Essential Tremor," Movement Disorders, vol. 16, No. 5, 2001, pp. 914-920.
Louis, E.D., et al., "How common is the most common adult movement disorder? Estimates of the prevalence of essential tremor throughout the world," Movement Disorders, 1998, 2 pages.
Mario Manto, et al., "Dynamically Responsive Intervention for Tremor Suppression," IEEE Engineering in Medicine and Biology Magazine, 2003, 22(3):120-132.
Mark Heath, et al., "Design Considerations in Active Orthoses for Tremor Suppression: Ergonomic Aspects and Integration of Enabling Technologies," Assistive Technology—Shaping the Future AAATE, 2003, p. 842-846.
Mitchell F. Brin, et al., "Epidemiology and Genetics of Essential Tremor," Movement Disorders 13(S3):55-63, 1998.
National Parkinson Foundation, Treatment options, 2009, <http://www.parkinson.org/Parkinson-s-Disease/Treatment >, 1 page.
Olivier W. Bertacchini, et al., "Fatigue life characterization of shape memory alloys undergoing thermomechanical cyclic loading," Smart Structures and Materials 2003, 2003. 5053:612-624.
Pathak et al. "Dynamic characterization and single-frequency cancellation performance of SMASH (SMA actuated stabilizing handgrip)," In: "Modeling, Signal Processing, and Control for Smart Structures," Proceedings of SPIE, vol. 6926, 2008, pp. 692602-1-692602-12, <http://144.206.159.178/ft/CONF/16413457/16413459.pdf> [retrieved Nov. 26, 2012], entire document.
Pathak, A. et al. "A Noninvasive Handheld Assistive Device To Accommodate Essential Tremor: A Pilot Study," Brief Report, Movement Disorders, May 2014; 29(6):838-842. doi: 10.1002/mds.25796.
Pathak, A. et al., "Measurement and Collection of Human Tremors Through a Handheld Tool," U.S. Appl. No. 14/627,893, filed Feb. 20, 2015, whole document.
PCT/US2012/057048—International Search Report and Written Opinion of the International Searching Authority, dated Dec. 17, 2012.
PCT/US2012/057048, PCT International Preliminary Report on Patentability, dated Apr. 1, 2014, 5 pages.
PCT/US2014/045409—International Search Report and Written Opinion of the International Searching Authority, dated Nov. 3, 2014, 9 pages.
PCT/US2014/045409, PCT International Preliminary Report on Patentability, dated Jan. 14, 2016, 8 pages.
PCT/US2015/025781—International Preliminary Report on Patentability, dated Nov. 3, 2016, 9 pages.
PCT/US2015/025781—International Search Report and Written Opinion of the International Searching Authority, dated Jul. 1, 2015.
PCT/US2016/013704—International Search Report and Written Opinion, dated Apr. 6, 2016, 19 pages.
Pedley, Mark, "Tilt Sensing Using a Three-Axis Accelerometer," Freescale Semiconductor, Inc. Application Note, Document No. AN3461, Rev. 6, Mar. 2013, 22 pages.
Rodger J. Elble, "Physiologic and essential tremor," Neurology, 1986, 36(2):225-231.
Rodger J. Elble, et al., "Essential tremor frequency decreases with time," Neurology, 2000, 55(10):1547-1551.
Rubia P Meshack, et al., "A randomized controlled trial of the effects of weights on amplitude and frequency of postural hand tremor in people with Parkinson's disease," Clinical Rehabilitation, 2002, 16(5):481-492.
Sharon Smaga, "Tremor," American Family Physician, vol. 68, No. 8, Oct. 15, 2003, p. 1545-1552.
Shaw et al. "A reduced-order thermomechanical model and analytical solution for uniaxial shape memory alloy wire actuators," In: "Smart Materials and Structures," vol. 18, 2009, pp. 1-21, <http://deepblue.lib.umich.edu/bitstream/2027.42/65088/2/ sms9_6_065001.pdf>, entire document, especially Fig 1b; p. 3, col. 1 [retrieved Nov. 26, 2012].
U.S. Appl. No. 15/171,842, Anupam Pathak et al., filed Jun. 2, 2016.
U.S. Appl. No. 15/210,267, Anupam Pathak et al., filed Jul. 14, 2016.
U.S. Appl. No. 15/249,844, Anupam Pathak et al., filed Aug. 29, 2016.
Umemura, A. et al., "Deep Brain Stimulation for Movement Disorders: Morbidity and Mortality in 109 Patients," J Neurosurg 98: 779-784, 2003.
U.S. Appl. No. 13/250,000—Final Office Action, dated Mar. 20, 2014, 11 pages.
U.S. Appl. No. 13/250,000—Non-Final Office Action, dated Apr. 2, 2015, 19 pages.
U.S. Appl. No. 13/250,000—Non-Final Office Action, dated Apr. 5, 2013, 11 pages.
U.S. Appl. No. 13/250,000—Non-Final Office Action, dated Apr. 6, 2016, 13 pages.
U.S. Appl. No. 13/250,000—Non-Final Office Action, dated Oct. 19, 2016, 9 pages.
U.S. Appl. No. 13/250,000—Notice of Allowance, dated Oct. 1, 2015, 5 pages.
U.S. Appl. No. 13/250,000—Restriction Requirement, dated Dec. 19, 2012, 9 pages.
U.S. Appl. No. 13/935,387—Final Office Action, dated Oct. 21, 2016, 10 pages.
U.S. Appl. No. 13/935,387—Non-Final Office Action, dated Apr. 3, 2015, 25 pages.
U.S. Appl. No. 13/935,387—Non-Final Office Action, dated Apr. 12, 2017, 13 pages.
U.S. Appl. No. 13/935,387—Non-Final Office Action, dated Apr. 6, 2017, 14 pages.
U.S. Appl. No. 13/935,387—Notice of Allowance, dated Oct. 7, 2015, 5 pages.
Wireless & Mobile Human Monitoring, Latency Tech Note—Wireless Physiological Monitoring, Motion Sensor Latencies for Software Development, <http://glneurotech.com/bioradio/latency-tech-note/> [retrieved from Internet Feb. 3, 2015], 4 pages.
Wireless & Mobile Human Monitoring, Wireless motion sensor for 3D data acquisition via Bluetooth technology, Wireless Motion Sensor, <http://glneurotech.com/bioradio/physiological-signal-monitoring/wireless-motion-sensor/> [retrieved from Internet Feb. 3, 2015], 3 pages.
Chinese Office Action, dated Apr. 2, 2021, in corresponding Chinese Patent Application No. 201880028557.2, 9 pages.

(56) References Cited

OTHER PUBLICATIONS

Extended European Search Report, dated Jan. 13, 2021, in corresponding European patent Application No. 18793994.7, 7 pages.

* cited by examiner

HANDHELD ARTICULATED USER-ASSISTIVE DEVICE WITH BEHAVIOR CONTROL MODES

CROSS-REFERENCE TO RELATED APPLICATIONS

This application is a divisional of U.S. application Ser. No. 15/583,482, filed on May 1, 2017, which is hereby incorporated by reference.

TECHNICAL FIELD

This disclosure relates generally to handheld tools for people with limited upper-extremity mobility.

BACKGROUND INFORMATION

Millions of people suffer from disorders that may limit their upper-extremity mobility. These disorders include diseases such as cerebral palsy, spinal cord injuries, Huntington's Disease, or otherwise. Currently, there are limited solutions for those suffering from these disorders. Many rely on external assistance to perform activities of daily living including feeding, cooking, or grooming. There is a strong unmet need to provide assistance to these people to improve overall independence. Increased independence reduces caregiver costs and is associated with more positive long-term health outcomes.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system, apparatus, and method of operation for a handheld tool with behavior control modes are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1A:
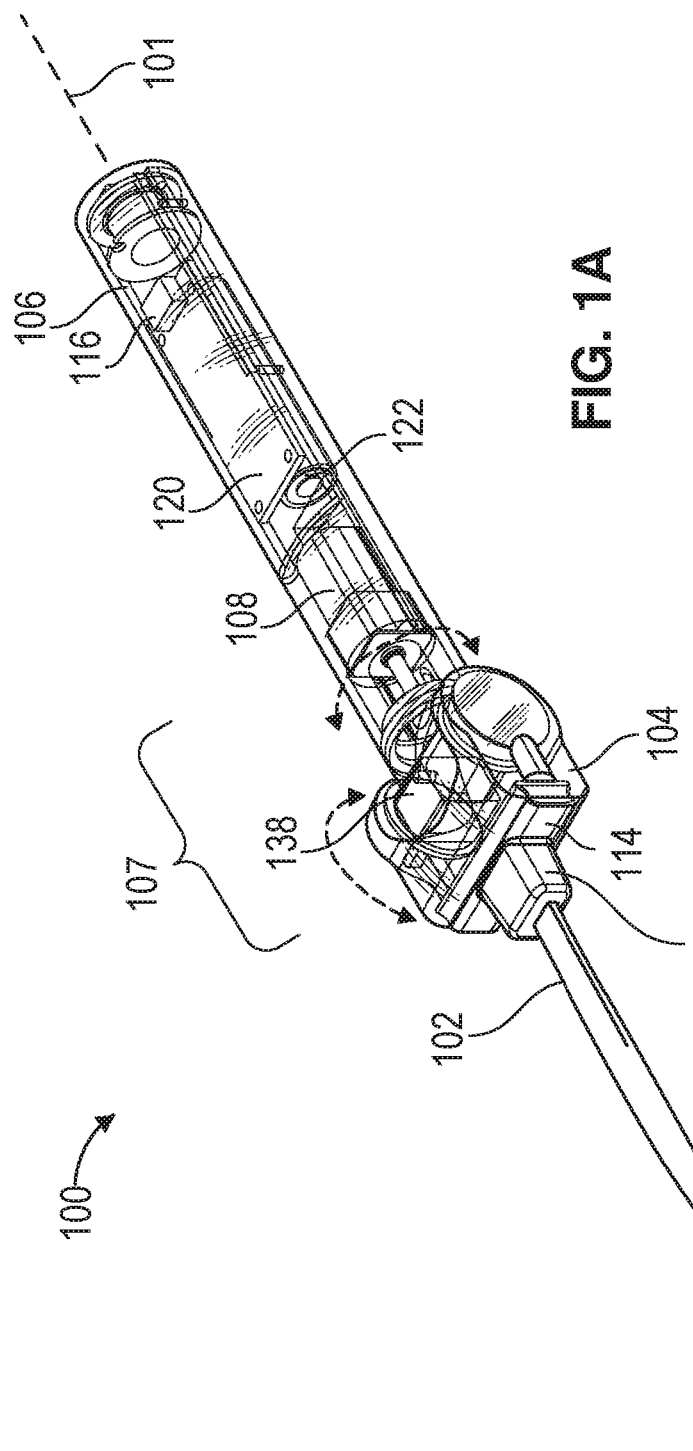
FIG. 1A is a perspective view illustration of a handheld tool that assists a user having mobility issues perform one or more tasks, in accordance with an embodiment of the disclosure.

FIG. 1A is a perspective view illustration of a handheld tool 100, in accordance with an embodiment of the disclosure. Handheld tool 100 is an articulated user-assistive device having different behavior control modes associated with different user-assistive implements (a demonstrative makeup applicator implement is illustrated in FIG. 1A). Each behavior control mode has a separate behavior routine stored in handheld tool 100 that aides users having limited upper-extremity mobility perform certain daily tasks. For example, these tasks may include personal grooming (e.g., applying makeup, brushing teeth, etc.), cooking, eating, drinking, or otherwise. The illustrated embodiment of handheld tool 100 includes a user-assistive implement 102 (e.g., a makeup applicator is illustrated), an implement mount 104, a handle 106, an actuator assembly 107, sensors 114 and 116, a control module 120, and a power source 122. The illustrated embodiment of actuator assembly 107 includes motors 108 and 138.

Figure 3A:
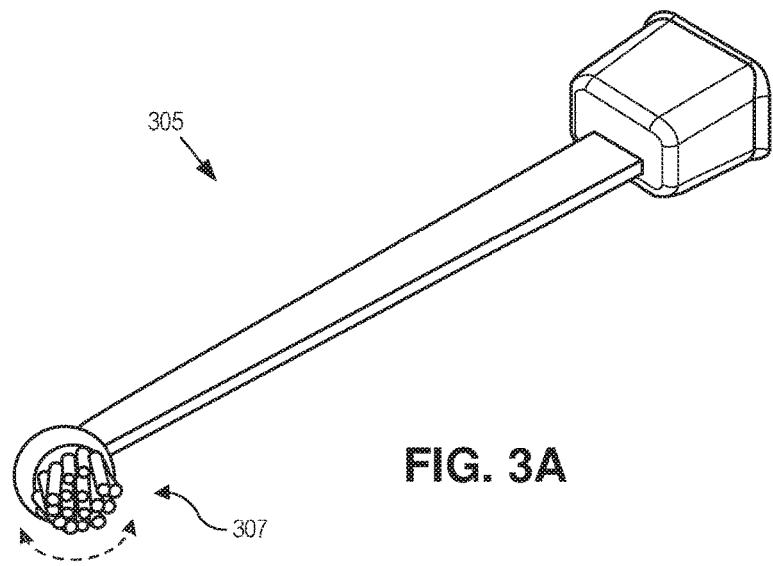
FIG. 3A is a perspective view illustration of a toothbrush implement for assisting a user while brushing teeth, in accordance with an embodiment of the disclosure.
Figure 3B:
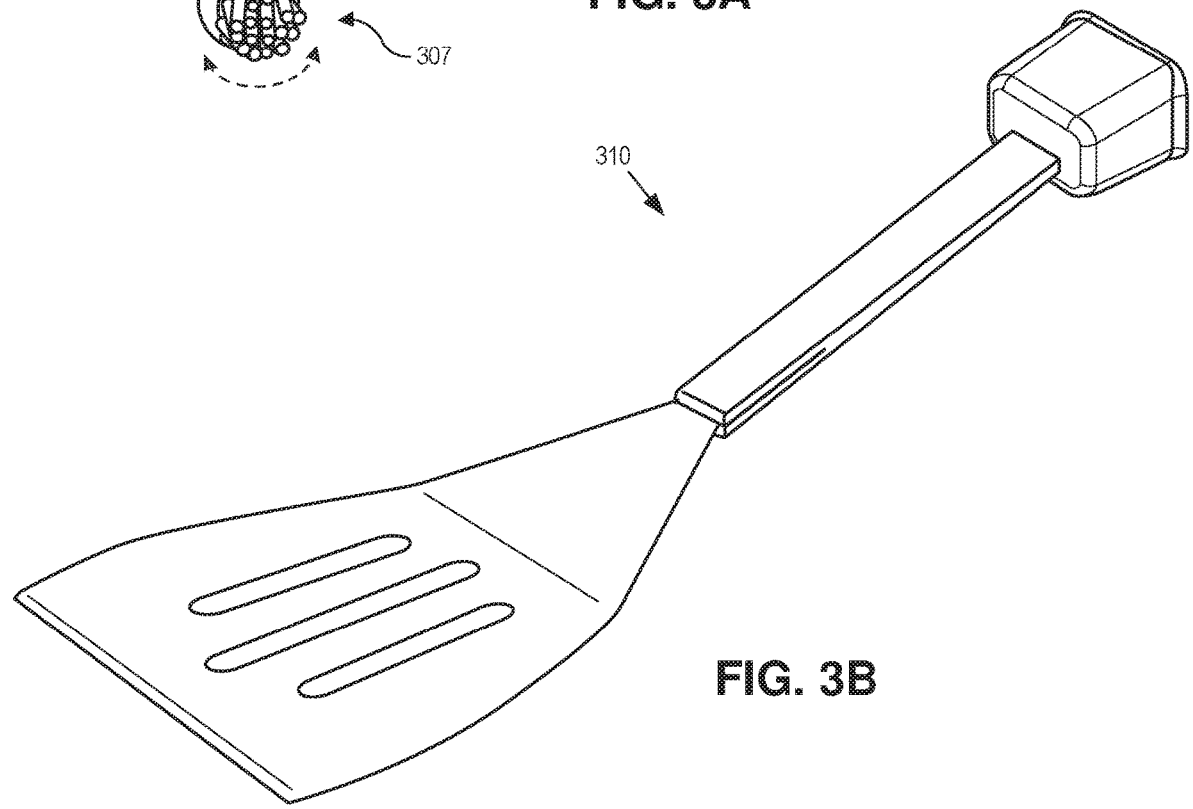
FIG. 3B is a perspective view illustration of a cooking utensil implement for assisting a user while cooking, in accordance with an embodiment of the disclosure.
Figure 3C:
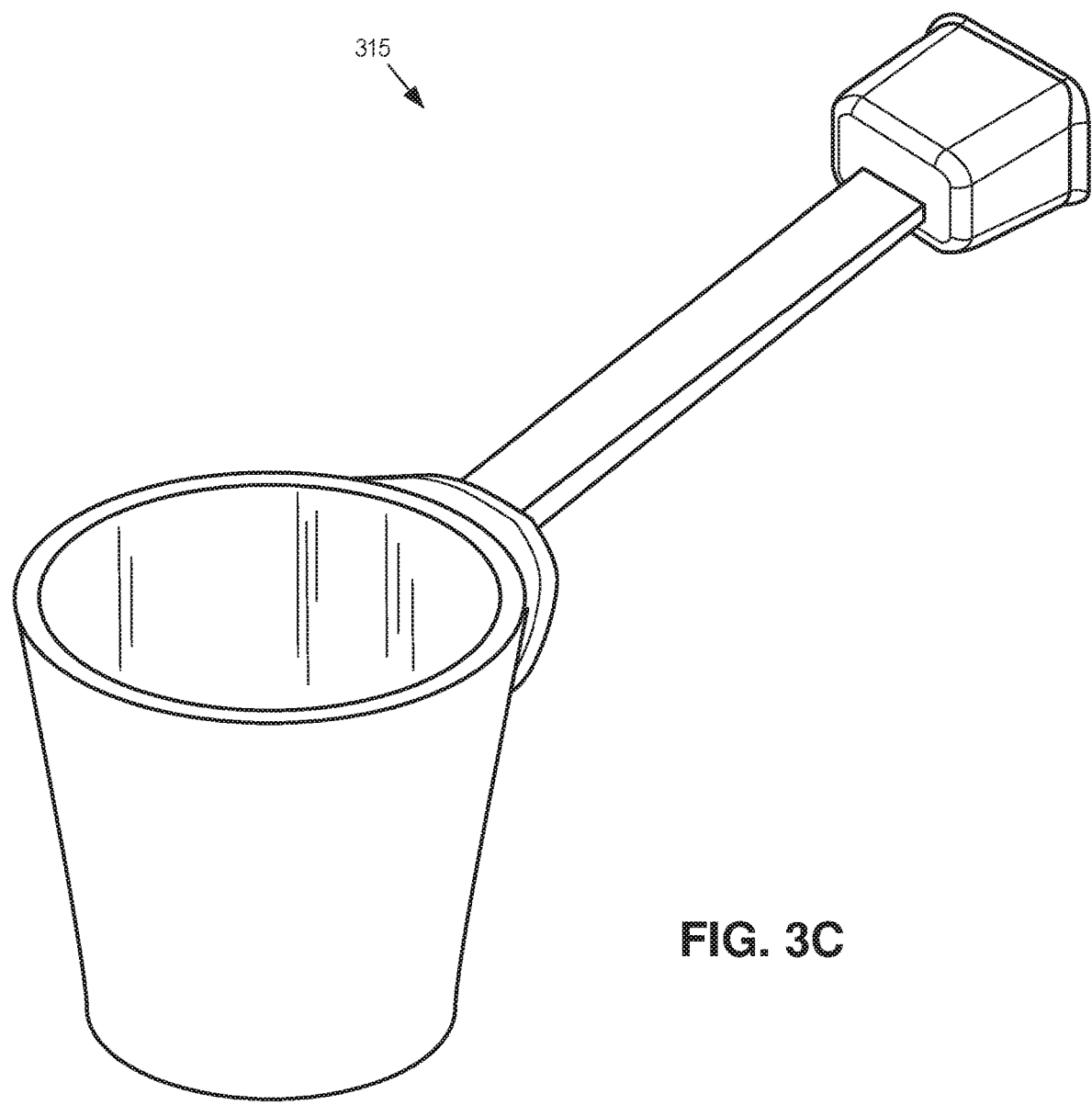
FIG. 3C is a perspective view illustration of a drink holder implement for assisting a user while drinking, in accordance with an embodiment of the disclosure.

FIGS. 3A-3C illustrate various other examples of a detachable user-assistive implement. For example, FIG. 3A illustrates a toothbrush implement 305, FIG. 3B illustrates a cooking utensil implement 310, and FIG. 3C illustrates a drink holder implement 315.

In the illustrated embodiment, implement mount 104 provides a detachable mount location for various types of user-assistive implements 102. In one embodiment, handle 106 and implement mount 104 are discrete rigid bodies of the handheld tool 100 connected by rotary joints of actuator assembly 107 that enable movement of implement mount 104, and thus user-assistive implement 102, in two rotational degrees of freedom relative to handle 106.

Handheld tool 100 is capable of independently detecting and tracking the absolute positions (relative to Earth's frame of reference) of handle 106 and user-assistive implement 102 using sensors 116 and 114, respectively. Control module 120 uses the real-time position/orientation data output from sensors 114 and 116 to control actuator assembly 107 to manipulate user-assistive implement 102 and aid the user perform one or more of the tasks described above, despite the user's limited mobility. In some embodiments, handheld tool 100 may even be capable of detecting and compensating (e.g., stabilizing) for unintentional muscle movement (e.g. tremors).

Handheld tool 100 includes handle 106, which also functions as a housing that contains various other subcomponents of handheld tool 100, such as power source 122, control module 120, and at least a portion of actuator assembly 107. Handheld tool 100 also includes implement mount 104 coupled to the housing 106 via actuator assembly 107, as discussed in greater detail below. Implement mount 104 is configured to accept a different user-assistive implements 102 (e.g., makeup applicator, toothbrush, cooking utensil, drink holder, etc.) to its end distal from handle 106.

Figure 1C:
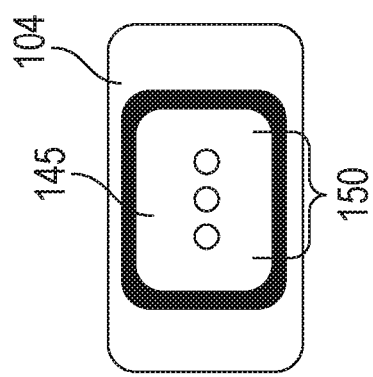
FIG. 1C is an illustration of an implement mount on a handheld tool for detachably connecting different user-assistive implements, in accordance with an embodiment of the disclosure.
Figure 1B:
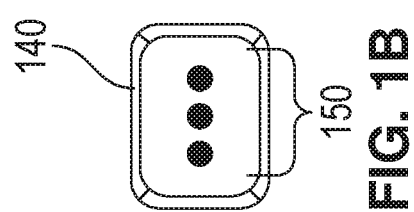
FIG. 1B is an illustration of a mounting end of a user-assistive implement that detachably connects the user-assistive implement to the handheld tool, in accordance with an embodiment of the disclosure.

In one embodiment, implement mount 104 uses one of a friction, snap, magnet, screw, or other form of locking mechanism to provide a detachable and rigid mounting point for user-assistive implements 102. FIG. 1B illustrates a mounting end 140 of user-assistive implement 102, while FIG. 1C illustrates the mounting interface 145 of implement mount 104. As illustrated both mounting interface 145 and mounting end 140 include contacts 150 that align with each and to form electrical contact when mounting end 140 is inserted into mounting interface 145. In one embodiment, electrical contacts 150 of mounting interface 145 are spring loaded pogo-pins that make physical contact with electrical contacts 150 within mounting end 140 of user-assistive implement 102. The illustrated embodiment includes three electrical contacts 150: a power contact, a ground contact, and a identifier (ID) contact. The power and ground contacts provide power to mechanized implements (e.g., electric toothbrush implement). In one embodiment, the ID contact of user-assistive implement 102 is coupled to a resistor having a resistance value that is interrogated by control module 120 to identify the type of user-assistive implement 102 that is currently attached. For example, control module 120 may store a plurality of behavior routines associated with a variety of different types of user-assistive implement ends 102. By measuring the resistance value of the ID contact and comparing the resistance value to a table of resistance values, the correct behavior routine may be loaded and executed. Other numbers of contacts (more or less) and physical form factors for the contacts may be used.

Figure 2A:
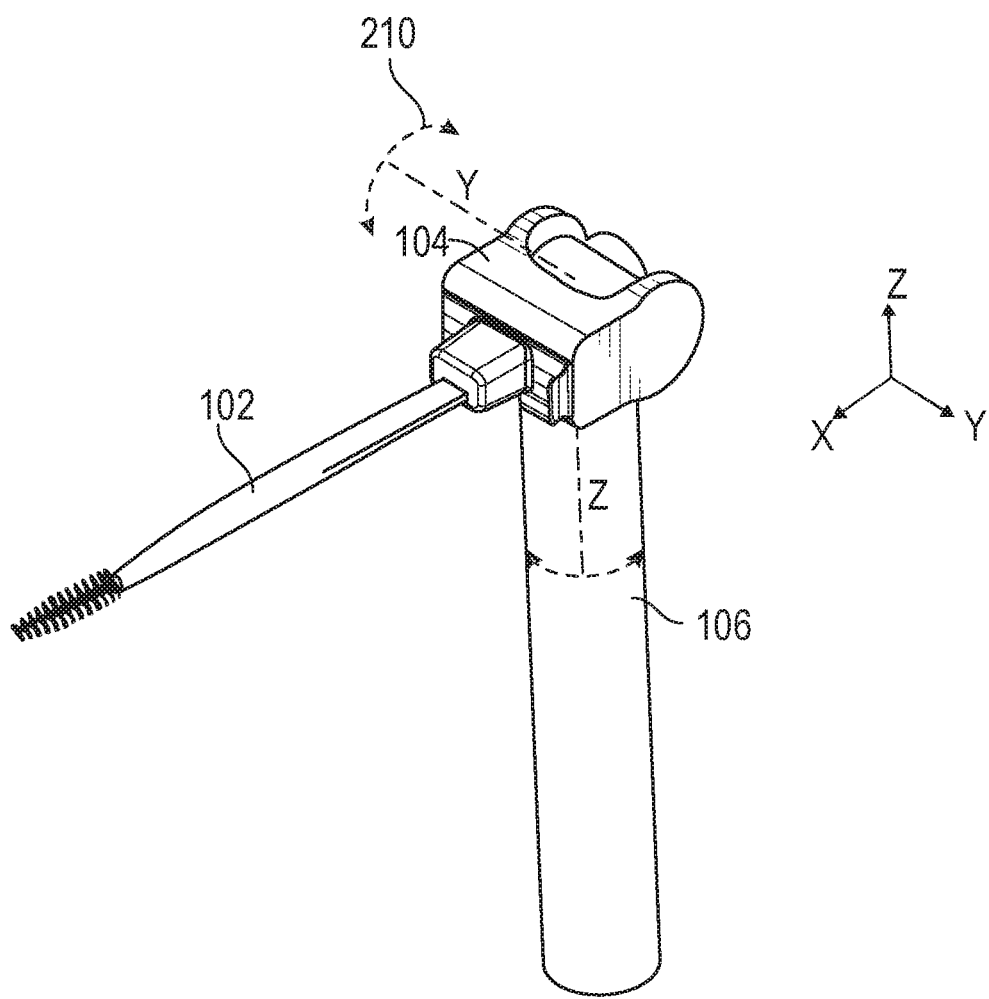
FIG. 2A is a perspective view illustration of the handheld tool and reference orientations of parts of the handheld tool, in accordance with an embodiment of the disclosure.
Figure 2B:
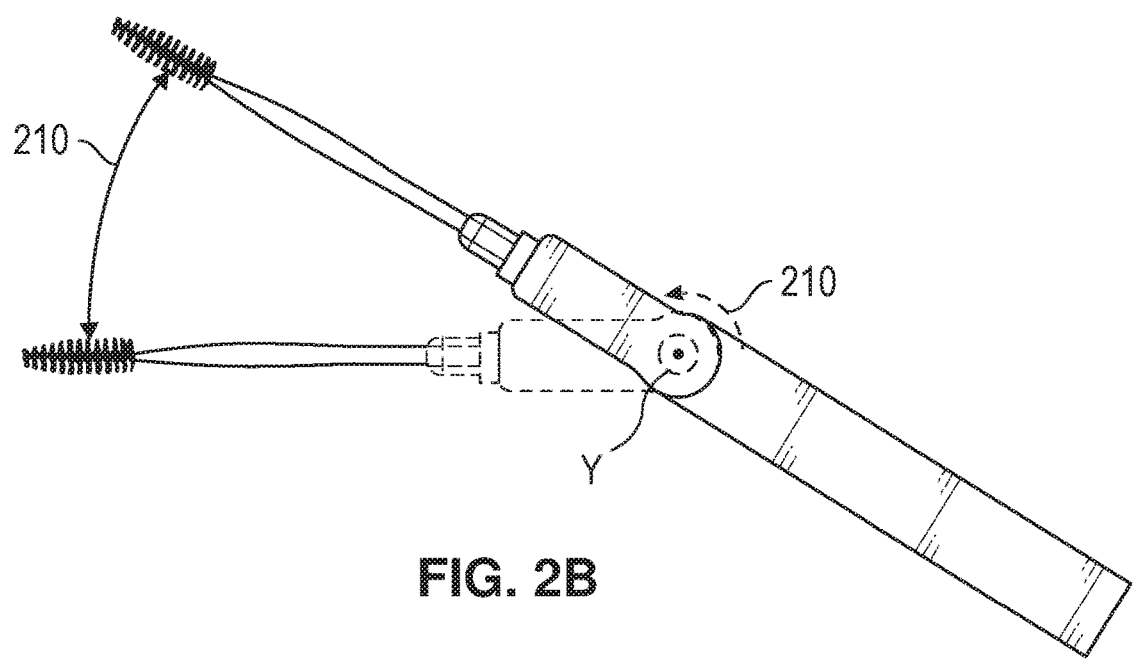
FIG. 2B is a perspective view illustration of a first type of motion of the handheld tool, in accordance with an embodiment of the disclosure.
Figure 2C:
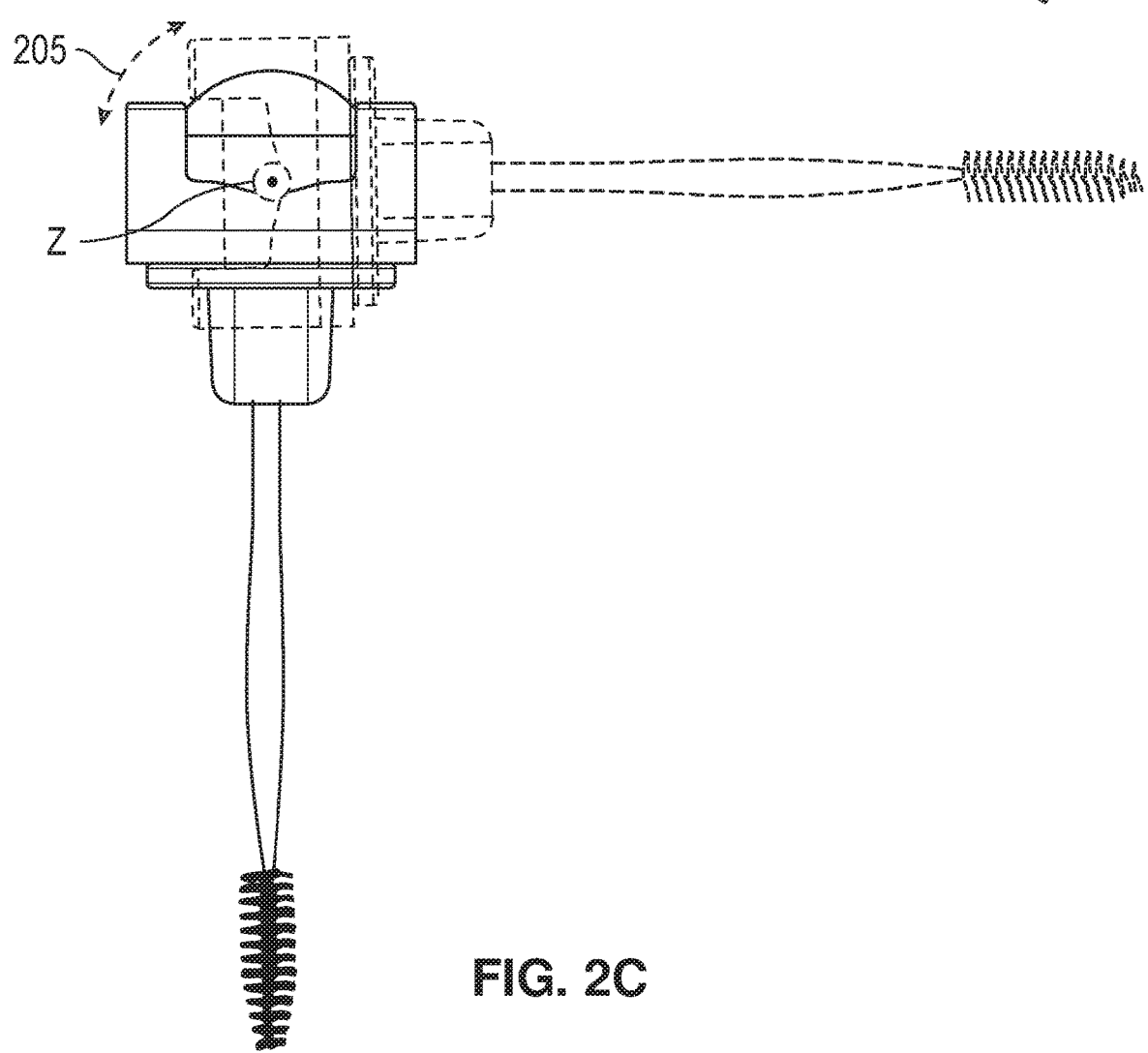
FIG. 2C is a perspective view illustration of a second type of motion of the handheld tool, in accordance with an embodiment of the disclosure.

As illustrated, implement mount 104 is coupled to the handle 106 via motors 108 and 138 of actuator assembly 107. Motor 108 is rigidly mounted to handle 106 and orientated to rotate both motor 138 and implement mount 104 in a first degree of freedom about rotational axis Z, as illustrated by movement 205 in FIG. 2C. Motor 138 connects the output of motor 108 to implement mount 104 and controls movement 210 of implement mount 104 in a second degree of freedom about a rotational axis Y, as illustrated in FIGS. 2A and 2B.

The illustrated embodiment of handheld tool 100 further includes at least two sensors (e.g., sensor 116 placed along or within handle 106 and sensor 114 placed along or within implement mount 104). In one embodiment, each of the sensors 116 and 114 are inertial measuring units (IMUs) capable of providing measurements of orientations, angular rate of movement, force, etc. of the bodies in which they are placed. In one embodiment, each IMU is a six degree of freedom IMU having at least an accelerometer and a gyroscope. In one embodiment, the sensors 116 and 114 respectively collect measurements during use of the handheld tool 100 to independently determine an orientation of the handle 106 and implement mount 104.

In embodiments, handheld tool 100 may further include a portable power source 122 to power the control module 120, actuator assembly 107, and powered user-assistive implements (e.g., toothbrush implement 305 in FIG. 3A). Power source 122 may utilize a variety of options including but not limited to a rechargeable battery, a solar panel, etc.

Sensors 114 and 116 take measurements to determine an orientation of handle 106 and an orientation of the implement mount 104 and/or implement 102. Control module 120, based on these two orientations, can determine the relative orientations of the parts of the handheld tool 100. Furthermore, the relative orientations of the parts can be used to determine the position of the joints that couple the handle 106 with the implement mount 104 and the current orientation of the user-assistive implement 102 relative to the handle 106. As will be discussed in greater detail below, based on the measured orientations and expected orientations between parts of the handheld tool 100, the control module 120 generates control signals (e.g., motor commands) for the actuator assembly 107 that correct and/or maintain an expected relative orientation between the different parts of handheld tool 100 or maintains an absolute orientation of user-assistive implement 102. These control signals can be manipulated according to various behavior routines to aid the user in the performance of various tasks associated with a given type of user-assistive implement 102. In one embodiment, the control signals may include voltage commands generated by control module 120 that drive the motors of the actuator assembly 107 to turn their respective gears in a desired direction, at a desired speed, with a desired acceleration, etc.

One of ordinary skill in the art readily recognizes that a system and method in accordance with the present disclosure may utilize various implementations of control module 120, sensors 114 and 116, actuator assembly 107, etc. that would be within the spirit and scope of the present disclosure. In one embodiment, control module 120 comprises an electrical system, capable of producing an electrical response from sensor inputs, such as a programmable microcontroller, a field-programmable gate array (FPGA), an application specific integrated circuit ("ASIC"), or otherwise. In one embodiment, control module 120 comprises an 8-bit ATMEGA8A programmable microcontroller manufactured by Atmel due to its overall low-cost, low-power consumption and ability to be utilized in high-volume applications.

Figure 4:
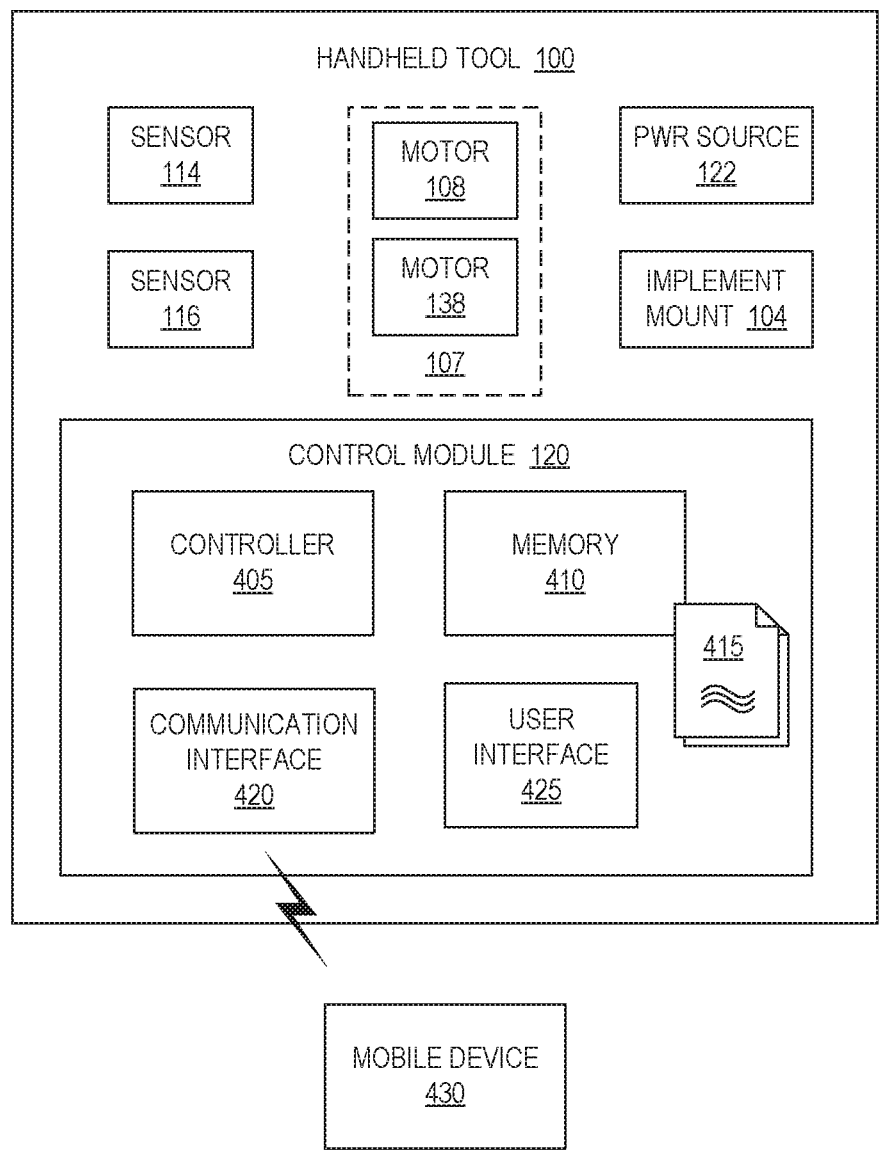
FIG. 4 is a functional block diagram illustrating subsystems of the handheld tool, in accordance with an embodiment of the disclosure.

FIG. 4 is a functional block illustration of various subsystems of handheld tool 100, in accordance with an embodiment of the disclosure. The illustrated embodiment of handheld tool 100 includes actuator assembly 107 including motors 108 and 138, sensors 114 and 116, power source 122, and control module 120. The illustrated embodiment of control module 120 includes a controller 405, memory 410 storing behavior routines 415, a communication interface 420, and a user interface 425.

As discussed above, controller 405 is coupled to sensors 114 and 116 to received orientation/motion information and output control signals for manipulating motors 108 and 138. The control signals are generated according to the instructions of behavior routines 415 stored in memory 410 with feedback from sensors 114 and 116. Communication interface 420 may include a wired connection (e.g., USB interface) or wireless connection (e.g., WiFi, Bluetooth, etc.). In one embodiment, communication interface 420 provides a wireless connection to a mobile device 430 (e.g., smart phone). The wireless connection can be used to receive user commands while executing behavior routines 415, provide software updates to controller 405, or update behavior routines 415. The user commands may be tactile inputs via a screen of mobile device 430 or voice commands. Communication interface 420 may also be used to communicate operational adjustments to handheld tool 100. For example, an application running on mobile device 430 may adjust a level of assistance applied to actuator assembly 107 as a user regains their upper extremity dexterity/mobility. A doctor or physical therapist may monitor assistance levels through cloud connectivity and remotely adjust assistance-level settings.

In one embodiment, control module 120 also provides an integrated user interface 425 to received direct user commands. User interface 425 may include one or more of a microphone for voice commands or a tactile interface (e.g., buttons, touch sensitive screen, pressure sensors to measure squeeze commands, etc.) for touch commands.

Figure 5:
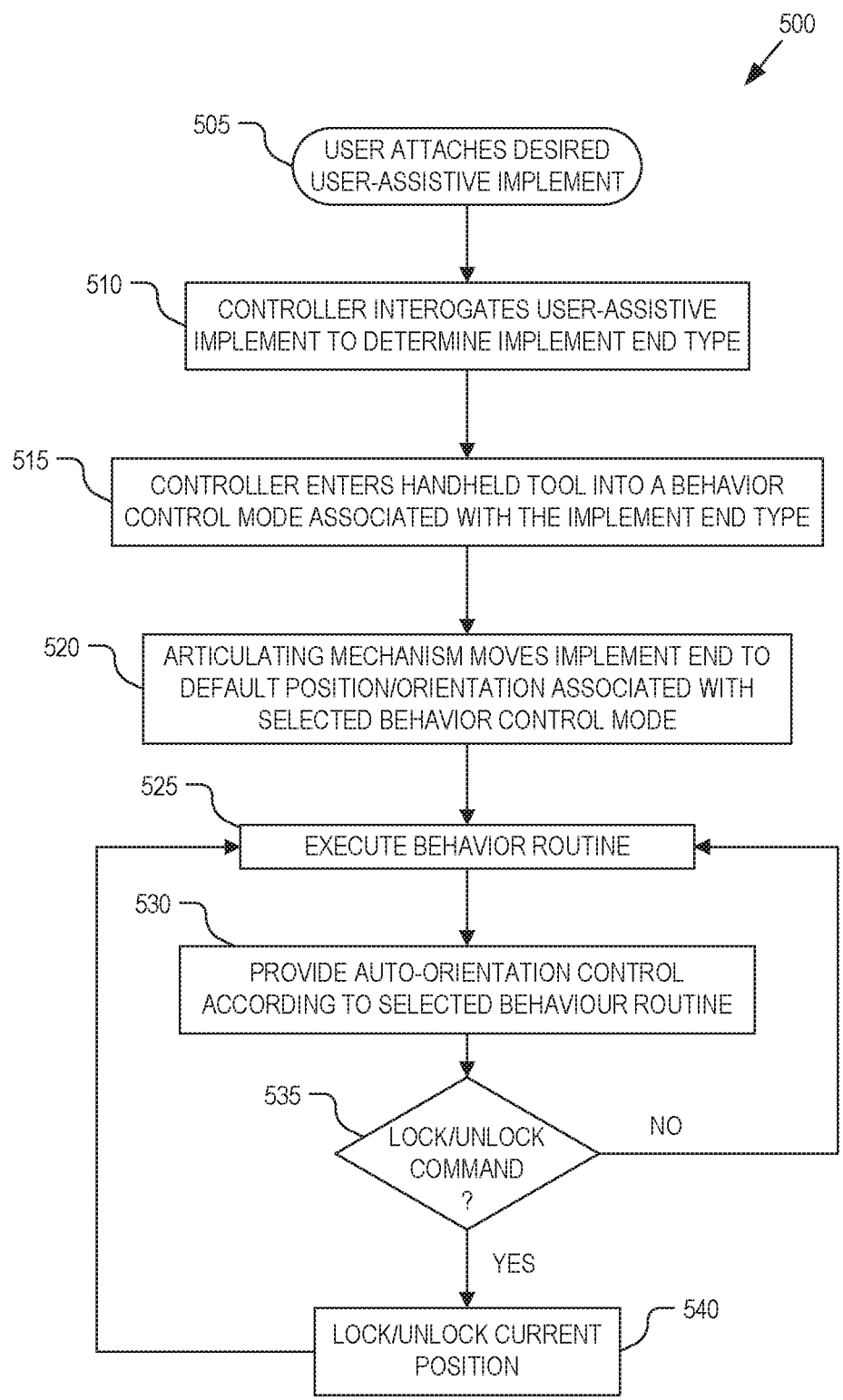
FIG. 5 is a flow chart illustrating general operation of the handheld tool, in accordance with an embodiment of the disclosure.

FIG. 5 is a flow chart illustrating a process 500 of general operation for handheld tool 100, in accordance with an embodiment of the disclosure. Process 500 is described with reference to functional elements of handheld tool 100 illustrated in FIGS. 1 and 4. The order in which some or all of the process blocks appear in process 500 should not be deemed limiting. Rather, one of ordinary skill in the art having the benefit of the present disclosure will understand that some of the process blocks may be executed in a variety of orders not illustrated, or even in parallel.

In a process block 505, the user attaches a desired user-assistive implement to mounting end 140. The selected user-assistive implement may include any one of user-assistive implements 102, 305, 310, 315, or otherwise. In process block 510, controller 405 interrogates the attached user-assistive implement to determine its type. In one embodiment, interrogation includes measuring a resistance value of a resistor disposed within the user-assistive implement through an ID contact (e.g., one of electrical contacts 150). The measured resistance value is then compared against a table of resistance values that correlates resistance values or ranges to different types of user-assistive implements. Once controller 405 determines the type of the connected user-assistive implement, handheld tool 100 is entered into a corresponding behavior control mode by loading and executing an associated behavior routine (process block 515).

In a process block 520, the articulating mechanisms of actuator assembly 107 move the user-assistive implement into a default position/orientation associated with the selected behavior control mode. In various embodiments, the default position may be an initial position/orientation, may depend upon the current orientation of handle 106 (e.g., is handle upright, inverted, near horizontal, etc.), and/or may including active feedback control (e.g., auto-leveling, auto-orientation control, etc.). In process block 530, the specific behavior routine associated with the type of user-assistive implement is executed. FIGS. 6-9 describe various examples of behavior routines associated with different types of user-assistive implements. However, in general, each behavior routine includes some form of auto-orientation control, which is tailored according to the specific use-case of a given user-assistive implement. Auto-orientation control may include auto-leveling, absolute orientation control in one or more degrees of freedom relative to Earth's frame of reference, and/or relative orientation control relative to handle 106.

In a decision block 535, controller 405 continuously monitors for a user lock/unlock command. Acknowledgment of a lock command causes the actuator assembly 107 to lock user-assistive implement (process block 540) either at its current orientation relative to handle 106 or move to a default lock position and hold that position relative to handle 106. Acknowledgement of an unlock commend (decision block 535) causes actuator assembly 107 to unlock the user-assistive implement (process block 540) and resume execution of the loaded behavior routine (process block 525). User commands may be acknowledged as an intentional shake. The output of sensor 116 and/or sensor 114 may be monitored and filtered by controller 405 to identify an intentional shack. In another embodiment, the commands may be received as a voice command with a microphone either integrated into handheld tool 100 (e.g., user interface 425) or using the microphone of a wirelessly connected mobile device 430. In yet other embodiments, any of the native interfaces of mobile device 430 may be used to receive user commands.

Figure 6:
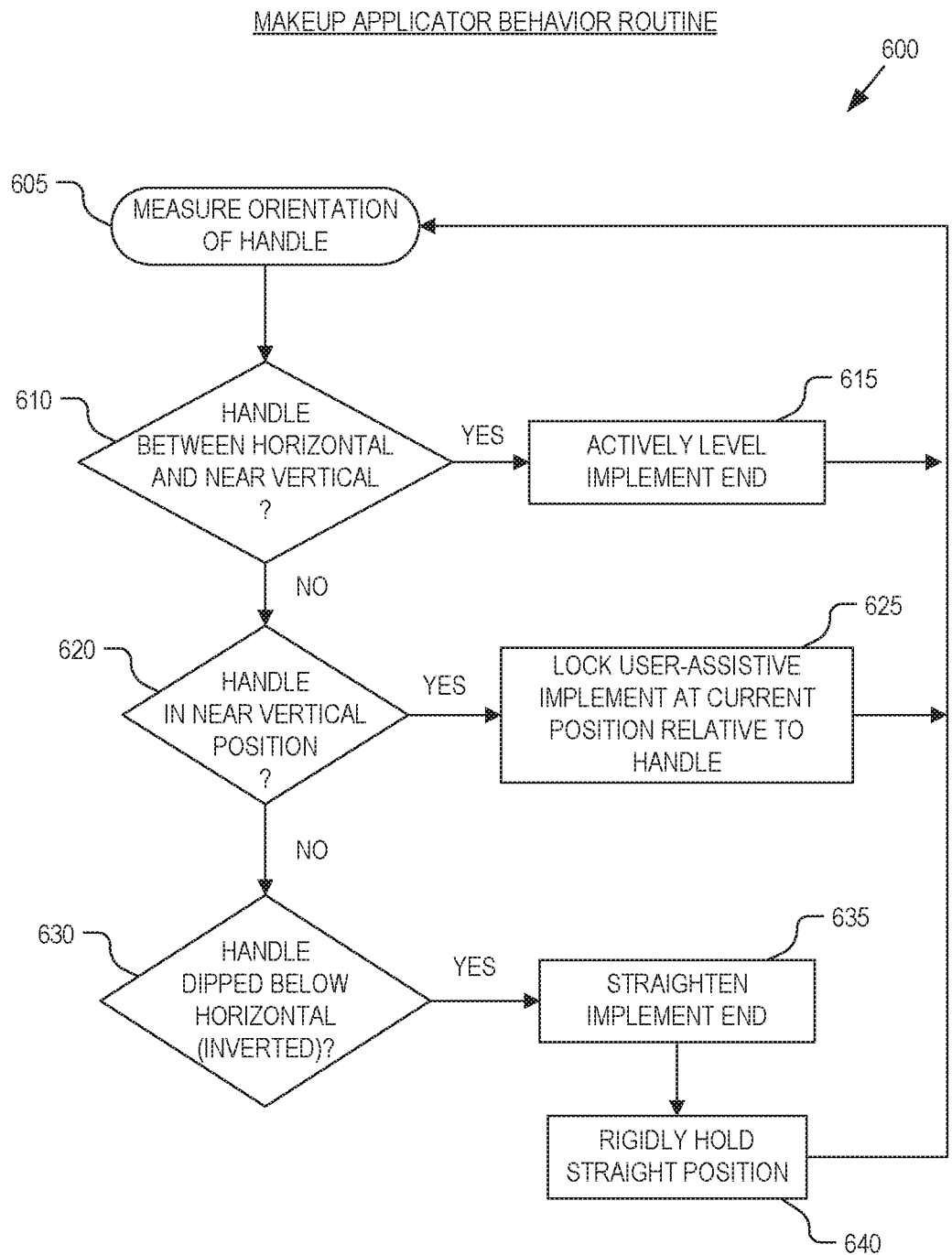
FIG. 6 is a flow chart illustrating a makeup applicator behavior routine, in accordance with an embodiment of the disclosure.

FIG. 6 is a flow chart illustrating a makeup applicator behavior routine 600 for use with a makeup applicator implement, in accordance with an embodiment of the disclosure. The order in which some or all of the process blocks appear in routine/process 600 should not be deemed limiting. Rather, one of ordinary skill in the art having the benefit of the present disclosure will understand that some of the process blocks may be executed in a variety of orders not illustrated, or even in parallel.

In a process block 605, controller 405 reads the output sensor 116 to continuously monitor the orientation of handle 106. In decision block 610, if handle 106 is determined to be between a horizontal position and a near vertical threshold position, then controller 405 operates actuator assembly 107 to actively level user-assistive implement 102. In one embodiment, the orientation of handle 106 is measured with reference to a longitudinal axis 101 extending down a centerline of handle 106. The near vertical threshold position may have a predetermined value (e.g., 15 degrees from vertical) or be a user defined value. Accordingly, despite a limited range of motion of handle 106 between the horizontal position and the near vertical threshold position, controller 405 operates actuator assembly 107 to ensure a center axis 103 of user-assistive implement 102 is maintained level at or near horizontal. However, if handle 106 is not between the horizontal position and the near vertical threshold position, then process 600 continues to decision block 620.

In decision block 620, if controller 405 determines that handle 106 is between the near vertical threshold position and an absolute vertical position, then the relative position between handle 106 and user-assistive implement 102 is locked (process block 625). In other words, the relative position between handle 106 and user-assistive implement 102 at the moment handle 106 crosses over the near vertical threshold position is held or locked for the time that handle 106 remains between absolute vertical and the near vertical threshold position. However, if handle 106 is not between the horizontal position and the absolute vertical position, then process 600 continues to a decision block 630.

In decision block 630, if handle 106 is dipped into an inverted position below the horizontal position (i.e., user-assistive implement 102 pointing downwards), then control module 120 operates actuator assembly 107 to straighten user-assistive implement 102 (process block 635). In other words, centerline axes 101 and 103 are aligned parallel to each other. Once straightened, actuator assembly 107 rigidly holds the straightened position until handle 106 rises above the horizontal position (process block 640). The straightening provided in process block 635, facilitates the user dipping user-assistive implement 102 into a makeup bottle, the active leveling provided in process block 615 facilitates level makeup application onto the body (e.g., eyelashes, eyebrows, eyelids, lips, etc.), and holding the locked position in process block 625 enables non-level makeup application.

Figure 7:
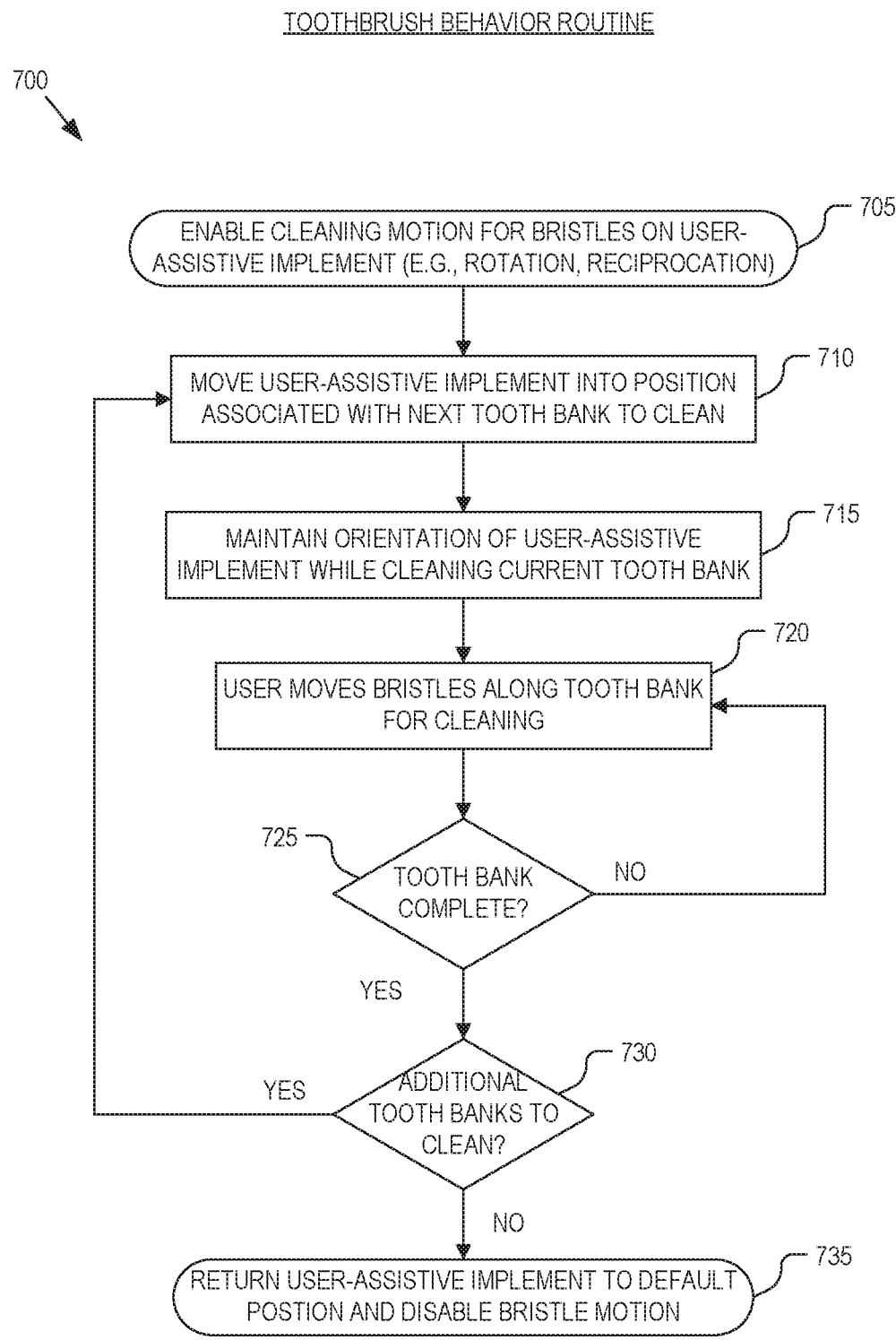
FIG. 7 is a flow chart illustrating a toothbrush behavior routine, in accordance with an embodiment of the disclosure.

FIG. 7 is a flow chart illustrating a toothbrush behavior routine 700 for use with toothbrush implement 305, in accordance with an embodiment of the disclosure. The order in which some or all of the process blocks appear in routine/process 700 should not be deemed limiting. Rather, one of ordinary skill in the art having the benefit of the present disclosure will understand that some of the process blocks may be executed in a variety of orders not illustrated, or even in parallel.

In a process block 705, controller 405 activates the cleaning motion for bristles 307 (see FIG. 3A) on toothbrush implement 305. In one embodiment, power is delivered to bristles 307 via electrical contacts 150. In a process block 710, toothbrush implement 305 is moved into a position associated with a first tooth bank to clean. A tooth bank is one side of a group of teeth that are cleaned using substantially the same handle orientation. For example, the outside of the upper-left row of teeth (e.g., upper left molars, bicuspids, lateral, and central) may correspond to one bank of teeth. In a process block 715, controller 405 operates actuator assembly 107 to maintain the correct orientation of toothbrush implement 305 while the current bank of teeth is cleaned. In process block 720, the user moves bristles 307 along the current tooth bank for cleaning. After the current tooth bank is cleaned (decision block 725), controller 405 moves toothbrush implement 305 to the next position/orientation associated with the next tooth bank (process 710). The completion of a given tooth bank may occur after experiation of fixed period of time (e.g., timer) or after receiving a user command to move to the next tooth bank. A user command may be received as a voice command, an intentional shake of handheld tool 100, or by other means. Cleaning and repositioning continue until all tooth banks have been cleaned (decision block 730). Once all tooth banks are cleaned, controller 405 returns toothbrush implement 305 to its default position and disables the bristle motion.

It should be appreciated that toothbrush behavior routine 700 may include orientation settings for a number of tooth bank positions. For example, the upper-left, upper-right, lower-left, and lower-right rows of teeth (each including molars, bicuspids, a lateral tooth, and a central tooth) may each have an inside and outside bank of teeth, corresponding to a total of eight banks of teeth. In other embodiments, the outside of the front teeth may correspond to yet a ninth bank of teeth while the inside of the upper-front and lower-front teeth may each correspond to additional banks for a total of eleven banks of teeth. The particular number of tooth banks may be customized or adjusted as desired.

Figure 8:
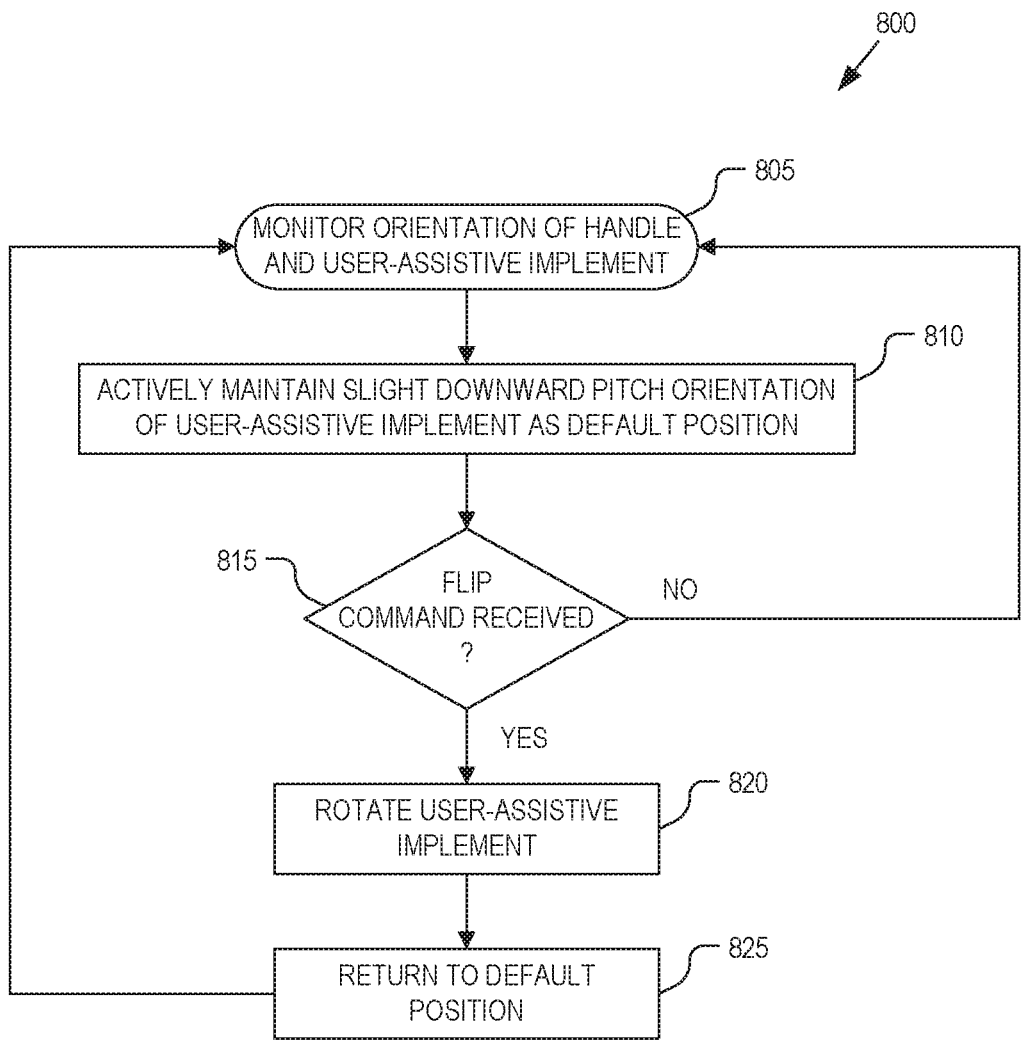
FIG. 8 is a flow chart illustrating a cooking utensil behavior routine, in accordance with an embodiment of the disclosure.

FIG. 8 is a flow chart illustrating a cooking utensil behavior routine 800 for use with cooking utensil implement 310, in accordance with an embodiment of the disclosure. The order in which some or all of the process blocks appear in routine/process 800 should not be deemed limiting. Rather, one of ordinary skill in the art having the benefit of the present disclosure will understand that some of the process blocks may be executed in a variety of orders not illustrated, or even in parallel.

In a process block 805, controller 405 uses the output of sensors 114 and 116 to monitor the orientation of handle 106 and cooking utensil implement 310. Based upon the feedback from sensors 114 and 116, controller 405 operates actuator assembly 107 to maintain a slight downward pitch orientation (e.g., 15-degrees below level) of cooking utensil implement 310 as a default position for routine 800 (process block 810). In one embodiment, the slight downward pitch orientation of cooking utensil implement 310 is maintained despite a relatively large deviation in the orientation of handle 106. This enables a user will relatively low upper-extremity motor control to achieve the correct orientation of cooking utensil implement 310 for sliding or scooping under food. Although FIG. 3B illustrates cooking utensil implement 310 as a spatula, it is anticipated that cooking utensil implement 310 may be a spoon or scoop, a fork, tongs, or otherwise.

With a food item on the end of cooking utensil implement 310, the user can issue a flip/rotate command to flip over the food. The command may be issued as a voice command, shaking or squeezing handle 106, via mobile device 430, or otherwise. In a decision block 815, controller 405 monitors for the flip command. Upon receipt of a flip command (decision block 815), controller 405 operates actuator assembly 107 to rotate cooking utensil implement 310 (process block 820) and turn over the food item. After rotating cooking utensil implement 310, controller 405 returns cooking utensil implement 310 to its default position.

Figure 9:
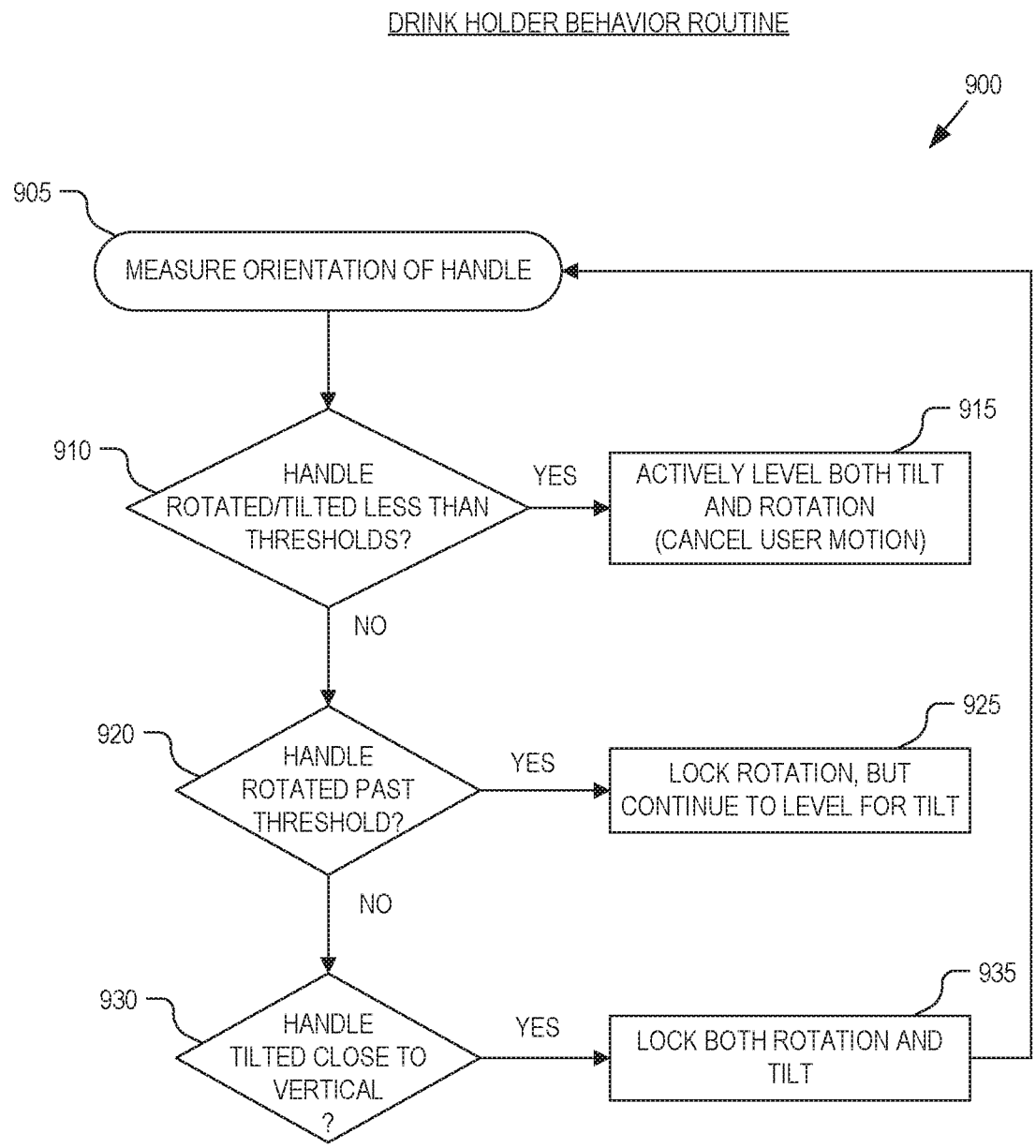
FIG. 9 is a flow chart illustrating a drink holder behavior routine, in accordance with an embodiment of the disclosure.

FIG. 9 is a flow chart illustrating a drink holder behavior routine for use with drink holder implement 315, in accordance with an embodiment of the disclosure. The order in which some or all of the process blocks appear in routine/process 900 should not be deemed limiting. Rather, one of ordinary skill in the art having the benefit of the present disclosure will understand that some of the process blocks may be executed in a variety of orders not illustrated, or even in parallel.

In a process block 905, controller 405 and sensor 116 continuously monitor the orientation of handle 106. In decision block 910, if handle 106 is rotated less than a rotational threshold and tilted less than tilting threshold, then the controller 405 operates actuator assembly 107 to actively level drink holder implement 315 in both rotational and tilt axes (process block 915). In other words, controller 405 acts to maintain a level drinking cup despite a user with limited upper-extremity control rotating or tilting handle 106 within prescribed thresholds. In some embodiments, the rotational and tilt axes are orthogonal rotational axis relative to handle 106. In other embodiments, the rotational and tilt axes are orthogonal rotational axis relative to drink holder implement 315.

If however, the user rotates handle 106 past the rotational threshold (decision block 920), then controller 405 operates actuator assembly 107 to lock the rotational position of drink holder implement 315 relative to handle 106 (process block 925). Thus, the rotational motion is a rotation towards the user's mouth. In one embodiment, the rotational axis is a 15-degree rotation towards the user's mouth. Accordingly, if the user rotates handle 106 past 15-degrees towards the user's mouth, then controller 405 stops actively leveling drink holder implement 315, locks its current rotational position upon crossing the threshold, and allows the user to rotate drink holder implement 315 for drinking. In one embodiment, just the rotational position is locked while continuing to actively level any tilting rotation. In another embodiment, both the rotational and tilt positions are locked.

If however, the user tilts handle 106 past a tilt threshold close to vertical (e.g., within 15-degrees of vertical or other threshold values whether greater or smaller), then controller 405 operates actuator assembly 107 to lock both the rotational position and the tilt position. Alternatively, the user may issue a locking command as discussed in connection with decision block 535 and process block 540 in general operation process 500.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. At least one machine-accessible storage medium that provides instructions that, when executed by a controller of a handheld tool, will cause the handheld tool to perform operations comprising:
   identifying a user-assistive implement attached to an implement mount disposed at an end of a handle of the handheld tool;
   manipulating the user-assistive implement relative to the handle with an actuator assembly mounted to the handle according to a behavior routine to aid a user while the user performs a task with the handheld tool;
   monitoring at least one motion sensor mounted in or on the handheld tool to identify an intentional shake of the handheld tool;
   locking the user-assistive implement in a current position when the intentional shake of the handheld tool is determined to have occurred; and
   unlocking the user-assistive implement to resume manipulating the user-assistive implement when another instance of the intentional shake is determined to have occurred.

2. The at least one machine-accessible storage medium of claim 1, wherein the operations further comprise:
   selecting the behavior routine from a plurality of different behavior routines stored in on-board memory of the handheld tool, each of the different behavior routines for aiding performance of a different task associated with each of a plurality of different types of user-assistive implements.

3. The at least one machine-accessible storage medium of claim 2, wherein manipulating the user-assistive implement relative to the handle according to the behavior routine comprises:
   automatically maintaining a fixed orientation of the user-assistive implement despite changes in orientation of the handle according to the behavior routine.

4. The at least one machine-accessible storage medium of claim 1, wherein the implement mount includes a first identifier contact that aligns to a second identifier contact on the user-assistive implement, and wherein identifying the user-assistive implement comprises:
   measuring a resistance value of a resistor disposed within the user-assistive implement through the first and second identifiers contacts;
   comparing the resistance value to a table of resistance values that correlates resistance values to types of user-assistive implements.

5. The at least one machine-accessible storage medium of claim 1, wherein the user-assistive implement comprises a toothbrush implement, the behavior routine comprises a toothbrush behavior routine for aiding a user while brushing teeth with the handheld tool, and manipulating the user-assistive implement according to the behavior routine comprises:
   activating a cleaning motion for bristles on the user-assistive implement;
   maintaining a current orientation of the user-assistive implement while cleaning a current bank of teeth of the user despite changes in orientation of the handle;
   adjusting the user-assistive implement to a next orientation for cleaning a next bank of teeth of the user; and
   repeating the maintaining and adjusting until all banks of teeth of the user have been cleaned.

6. The at least one machine-accessible storage medium of claim 1, wherein the user-assistive implement comprises a makeup applicator implement, the behavior routine comprises a makeup applicator behavior routine for aiding a user while applying facial makeup with the handheld tool, and manipulating the user-assistive implement according to the behavior routine comprises:
   continuously measuring an orientation of the handle;
   actively leveling the user-assistive implement when the handle is between a horizontal position and an angular threshold position;

holding a locked position of the user-assistive implement relative to the handle when the handle is between the angular threshold position and an absolute vertical position, the locked position being a position of the user-assistive implement upon crossing over the angular threshold position; and straightening the user-assistive implement into a straightened position that forms a straight line with the handle when the handle is dipped into an inverted position below the horizontal position.

7. The at least one machine-accessible storage medium of claim 1, wherein the user-assistive implement comprises a drink holder implement, the behavior routine comprises a drink holder behavior routine for aiding a user while drinking with the handheld tool, and manipulating the user-assistive implement according to the behavior routine comprises:

continuously measuring an orientation of the handle;

actively leveling the user-assistive implement when the handle is rotated less than a rotational threshold and tilted less than a tilt threshold from horizontal;

locking a rotational position of the user-assistive implement relative to the handle when the handle is rotated past the rotational threshold; and locking both the rotational position and a tilt position of the user-assistive implement relative to the handle when the handle is tilted past the tilt threshold.

8. The at least one machine-accessible storage medium of claim 1, wherein the user-assistive implement comprises a cooking utensil implement and the behavior routine comprises a cooking utensil behavior routine for aiding a user while flipping a food item with the handheld tool.

9. A method for assisting a user of a handheld tool, the method comprising: identifying, with a controller a type of user-assistive implement attached to an implement mount disposed at an end of a handle of the handheld tool;

Selecting, with the controller, a behavior routine based upon the type of the user-assistive implement identified;

manipulating the user-assistive implement relative to the handle with an actuator assembly mounted to the handle according to the behavior routine to aid the user while the user performs a task with the handheld tool, monitoring at least one motion sensor mounted in or on the handheld tool to identify an intentional shake of the handheld tool;

locking the user-assistive implement in a current position when the intentional shake of the handheld tool is determined to have occurred;

and unlocking the user-assistive implement to resume manipulating the user-assistive implement when another instance of the intentional shake is determined to have occurred.

10. The method of claim 9, wherein selecting the behavior routine comprises:

selecting, with the controller, the behavior routine from a plurality of different behavior routines stored in on-board memory of the handheld tool, each of the different behavior routines for aiding performance of a different task associated with each of a plurality of different types of user-assistive implements.

11. The method of claim 10, wherein manipulating the user-assistive implement relative to the handle according to the behavior routine comprises:

automatically maintaining a fixed orientation of the user-assistive implement despite changes in orientation of the handle according to the behavior routine.

12. The method of claim 9, wherein the implement mount includes a first identifier contact that aligns to a second identifier contact on the user-assistive implement, and wherein identifying the type of the user-assistive implement comprises:

measuring a resistance value of a resistor disposed within the user-assistive implement through the first and second identifiers contacts;

comparing the resistance value to a table of resistance values that correlates resistance values to types of user-assistive implements.

13. The method of claim 9, wherein the user-assistive implement comprises a toothbrush implement, the behavior routine comprises a toothbrush behavior routine for aiding a user while brushing teeth with the handheld tool, and manipulating the user-assistive implement according to the behavior routine comprises:

activating a cleaning motion for bristles on the user-assistive implement;

maintaining a current orientation of the user-assistive implement while cleaning a current bank of teeth of the user despite changes in orientation of the handle;

adjusting the user-assistive implement to a next orientation for cleaning a next bank of teeth of the user; and repeating the maintaining and adjusting until all banks of teeth of the user have been cleaned.

14. The method of claim 9, wherein the user-assistive implement comprises a makeup applicator implement, the behavior routine comprises a makeup applicator behavior routine for aiding a user while applying facial makeup with the handheld tool, and manipulating the user-assistive implement according to the behavior routine comprises:

continuously measuring an orientation of the handle;

actively leveling the user-assistive implement when the handle is between a horizontal position and an angular threshold position;

holding a locked position of the user-assistive implement relative to the handle when the handle is between the angular threshold position and an absolute vertical position, the locked position being a position of the user-assistive implement upon crossing over the angular threshold position; and straightening the user-assistive implement into a straightened position that forms a straight line with the handle when the handle is dipped into an inverted position below the horizontal position.

15. The method of claim 9, wherein the user-assistive implement comprises a drink holder implement, the behavior routine comprises a drink holder behavior routine for aiding a user while drinking with the handheld tool, and manipulating the user-assistive implement according to the behavior routine comprises:

continuously measuring an orientation of the handle;

actively leveling the user-assistive implement when the handle is rotated less than a rotational threshold and tilted less than a tilt threshold from horizontal;

locking a rotational position of the user-assistive implement relative to the handle when the handle is rotated past the rotational threshold; and locking both the rotational position and a tilt position of the user-assistive implement relative to the handle when the handle is tilted past the tilt threshold.

16. The method of claim 9, wherein the user-assistive implement comprises a cooking utensil implement and the behavior routine comprises a cooking utensil behavior routine for aiding a user while flipping a food item with the handheld tool.

17. At least one machine-accessible storage medium that provides instructions that, when executed by a controller of a handheld tool, will cause the handheld tool to perform operations comprising:
- identifying a type of user-assistive implement attached to an implement mount disposed at an end of a handle of the handheld tool;
- selecting a behavior routine based upon the type of the user-assistive implement identified; and
- manipulating the user-assistive implement relative to the handle with an actuator assembly mounted to the handle according to a behavior routine to aid a user while the user performs a task with the handheld tool,
- wherein the user-assistive implement comprises a makeup applicator implement, the behavior routine comprises a makeup applicator behavior routine for aiding a user while applying facial makeup with the handheld tool, and manipulating the user-assistive implement according to the behavior routine comprises:
  - continuously measuring an orientation of the handle;
  - actively leveling the user-assistive implement when the handle is between a horizontal position and an angular threshold position;
  - holding a locked position of the user-assistive implement relative to the handle when the handle is between the angular threshold position and an absolute vertical position, the locked position being a position of the user-assistive implement upon crossing over the angular threshold position; and
  - straightening the user-assistive implement into a straightened position that forms a straight line with the handle when the handle is dipped into an inverted position below the horizontal position.

18. At least one machine-accessible storage medium that provides instructions that, when executed by a controller of a handheld tool, will cause the handheld tool to perform operations comprising:
- manipulating a makeup applicator implement according to a makeup applicator behavior routine to aid a user with applying facial makeup with the handheld tool, wherein the makeup applicator implement is attached to an implement mount disposed at an end of a handle of the handheld tool and manipulated with an actuator assembly,
- wherein the makeup applicator behavior routine includes:
  - continuously measuring an orientation of the handle;
  - actively leveling the makeup applicator implement when the handle is between a horizontal position and an angular threshold position; and
  - holding a locked position of the makeup applicator implement relative to the handle when the handle is between the angular threshold position and an absolute vertical position, the locked position being a position of the makeup applicator implement upon crossing over the angular threshold position.

19. The at least one machine-accessible storage medium of claim 18, further providing instructions that, when executed by the controller, will cause the handheld tool to perform further operations, comprising:
- straightening the makeup applicator implement into a straightened position that forms a straight line with the handle when the handle is dipped into an inverted position below the horizontal position.

* * * * *